United States Patent
Justin

(10) Patent No.: US 7,494,490 B2
(45) Date of Patent: *Feb. 24, 2009

(54) APPARATUS AND METHOD FOR RECONSTRUCTING A LIGAMENT

(75) Inventor: Daniel F. Justin, Logan, UT (US)

(73) Assignee: DePuy Mitek, Inc., Raynham, MA (US)

( * ) Notice: Subject to any disclaimer, the term of this patent is extended or adjusted under 35 U.S.C. 154(b) by 342 days.

This patent is subject to a terminal disclaimer.

(21) Appl. No.: 10/964,590

(22) Filed: Oct. 13, 2004

(65) Prior Publication Data
US 2005/0065527 A1    Mar. 24, 2005

Related U.S. Application Data

(63) Continuation of application No. 09/792,168, filed on Feb. 22, 2001, now Pat. No. 6,808,528.

(60) Provisional application No. 60/184,292, filed on Feb. 23, 2000.

(51) Int. Cl.
*A61B 17/58* (2006.01)
(52) U.S. Cl. .......................... 606/96; 606/104
(58) Field of Classification Search .................. 606/72, 606/88, 99, 60, 62, 64, 65, 66, 300, 301, 606/96, 98, 103, 104, 148, 228; 128/898; 623/13.11–13.14
See application file for complete search history.

(56) References Cited

U.S. PATENT DOCUMENTS 5,139,520 A    8/1992    Rosenberg
5,266,075 A  * 11/1993  Clark et al. ................. 606/138
5,350,380 A  *  9/1994  Goble et al. .................. 606/80
5,393,302 A  *  2/1995  Clark et al. .................... 606/72
5,431,651 A     7/1995  Goble
5,570,706 A    11/1996  Howell
5,601,562 A     2/1997  Wolf et al.
5,603,716 A     2/1997  Morgan et al.
5,918,604 A  *  7/1999  Whelan ...................... 128/898
6,056,752 A  *  5/2000  Roger ..................... 623/13.12
6,123,710 A     9/2000  Pinczewski et al.

(Continued)

FOREIGN PATENT DOCUMENTS

WO        WO 99/15095        4/1999

*Primary Examiner*—Eduardo C Robert
*Assistant Examiner*—Tara R George
(74) *Attorney, Agent, or Firm*—Nutter McClennen & Fish LLP

(57) ABSTRACT

Apparatus and method is disclosed for securing a graft ligament in a bone tunnel. A method is disclosed comprising the steps of forming a first bone tunnel and a second bone tunnel being transverse to, and intersecting one another; positioning a closed loop of a flexible member within the first bone tunnel and a portion of the second bone tunnel such that the closed loop extends out of the first bone tunnel and the second bone tunnel, parting the closed loop outside the second bone tunnel so as to create a first free end and a second free end, and passing the second free end through the opposite end of second bone tunnel, and positioning the graft ligament over a portion of the flexible member extending out of the first opening; and pulling the flexible member so as to draw the graft ligament into the first bone tunnel.

6 Claims, 22 Drawing Sheets

U.S. PATENT DOCUMENTS

| | | |
|---|---|---|
| 6,132,433 A | 10/2000 | Whelan |
| 6,280,472 B1 | 8/2001 | Boucher et al. |
| 6,325,804 B1 | 12/2001 | Wenstrom et al. |
| 6,379,384 B1 | 4/2002 | McKernan et al. |
| 6,436,100 B1 | 8/2002 | Berger |
| 6,808,528 B2 * | 10/2004 | Justin .......................... 606/72 |

* cited by examiner

APPARATUS AND METHOD FOR RECONSTRUCTING A LIGAMENT

REFERENCE TO PENDING PRIOR PATENT APPLICATION

This is a continuation of prior U.S. patent application Ser. No. 09/792,168, filed Feb. 22, 2001 now U.S. Pat. No. 6,808,528 by Daniel F. Justin for APPARATUS AND METHOD FOR RECONSTRUCTING A LIGAMENT, which in turn claims benefit of prior U.S. Provisional Patent Application Ser. No. 60/184,292, filed Feb. 23, 2000 by Daniel F. Justin for METHOD OF DELIVERING AN ACL GRAFT. The above-identified patent applications are hereby incorporated herein by reference.

FIELD OF THE INVENTION

This invention relates to medical devices and procedures in general, and more particularly to medical devices and procedures for reconstructing a ligament.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause significant pain.

Various procedures have been developed to repair or replace a damaged ligament. The specific procedures used depend on the particular ligament which is to be restored and on the extent of the damage.

One ligament which is frequently damaged as the result of injury and/or accident is the anterior cruciate ligament (ACL). Looking now at FIG. 1, the ACL 5 extends between the top of the tibia 10 and the bottom of the femur 15. A damaged ACL can cause instability of the knee joint and cause substantial pain and arthritis.

Numerous procedures have been developed to restore the ACL through a graft ligament replacement. In general, and looking now at FIG. 2, these ACL replacement procedures involve drilling a bone tunnel 20 through tibia 10 and up into femur 15. Then a graft ligament 25, consisting of a harvested or artificial ligament or tendon(s), is passed through the tibial portion 30 of tunnel 20 (sometimes referred to as "the tibial tunnel"), across the interior of the joint, and up into the femoral portion 35 of tunnel 20 (sometimes referred to as "the femoral tunnel"). Then a distal portion of graft ligament 25 is secured in femoral tunnel 35, and a proximal portion of graft ligament 25 is secured in tibial tunnel 30.

There are numerous ways in which graft ligament 25 may be positioned in tunnel 20 and secured in position. However, none of the prior art apparatus and methods has proven to be entirely satisfactory, for a variety of reasons.

SUMMARY OF THE INVENTION

As a result, one object of the present invention is to provide improved apparatus for reconstructing a ligament.

And another object of the present invention is to provide an improved method for reconstructing a ligament.

These and other objects of the present invention are addressed by a novel apparatus and method for reconstructing a ligament.

In one preferred form of the invention, the invention comprises a method for securing a graft ligament in a bone tunnel, the method comprising the steps of: (1) forming a first bone tunnel in a bone, the first bone tunnel having a first opening at one end thereof, and forming a second bone tunnel in the same bone, the second bone tunnel being transverse to, and intersecting, the first bone tunnel, the second bone tunnel having first and second portions extending from the first bone tunnel, the first portion of the second bone tunnel having a second opening at one end thereof, and the second portion of the second bone tunnel having a third opening at one end thereof; (2) positioning a closed loop of a flexible member within the first bone tunnel and the first portion of the second bone tunnel such that a first portion of the closed loop extends out of the first opening and a second portion of the closed loop extends out of the second opening, parting the closed loop outside the second opening so as to create a first free end and a second free end, and passing the second free end through the second bone tunnel so that the second free end extends out of the third opening, and positioning the graft ligament over a portion of the flexible member extending out of the first opening; and (3) pulling the first and second free ends of the flexible member so as to draw the graft ligament into the first bone tunnel.

In another form of the invention, the invention comprises a system for securing a graft ligament in a bone tunnel, the system comprising a flexible member for positioning the graft ligament in the bone tunnel, the flexible member comprising a closed loop; an inserter for positioning a first portion of the closed loop in the bone tunnel; and a passing pin for withdrawing the first portion of the closed loop from the inserter positioned in the bone tunnel and pulling that portion of the closed loop through a portion of a second bone tunnel which intersects, and extends traverse to, the first-mentioned bone tunnel.

An in another form of the invention, the invention comprises a system for securing a graft ligament in a bone tunnel, the system comprising a flexible member extending through a second bone tunnel which intersects, and extends traverse to, the bone tunnel, the second bone tunnel having a first opening and a second opening, the flexible member having a first free end extending out of the first opening and a second free end extending out of the second opening, and wherein the graft ligament is looped over the flexible member; a cannulated crosspin mounted on the flexible member external to the first opening; a cannulated driver mounted on the flexible member outboard of the cannulated crosspin; and a cannulated bead mounted on the flexible member outboard of the cannulated driver, the cannulated bead having a larger outside diameter than the inside lumen of the cannulated driver; whereby, when tension is applied to the second end of the flexible member, the cannulated driver may be used to pass the cannulated crosspin beneath the graft ligament.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

The present invention comprises a novel apparatus and method for reconstructing a ligament.

Figure 1:
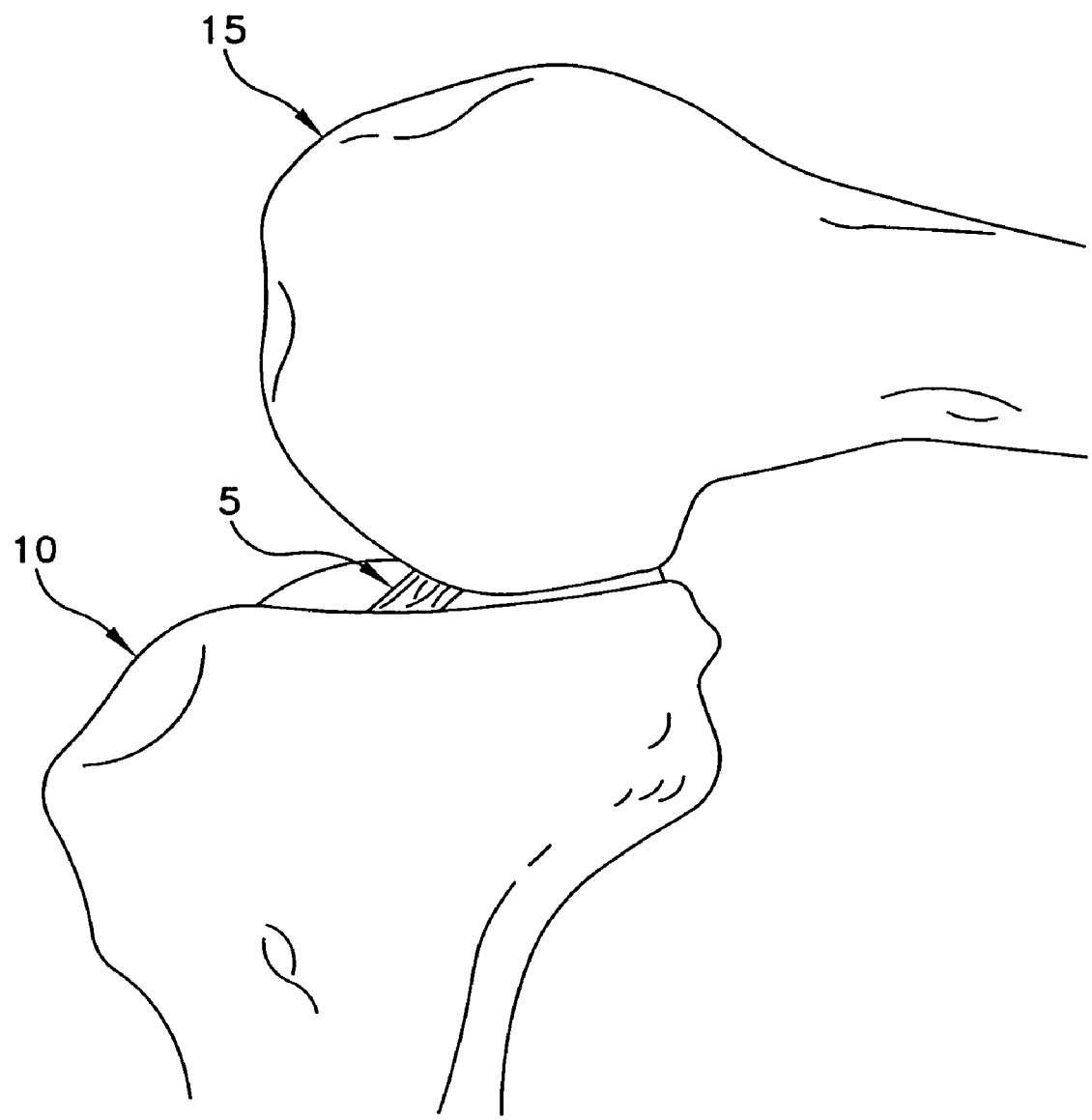
FIG. 1 is a schematic side view of a knee joint, showing an ACL extending between the top of the tibia and the bottom of the femur.
Figure 2:
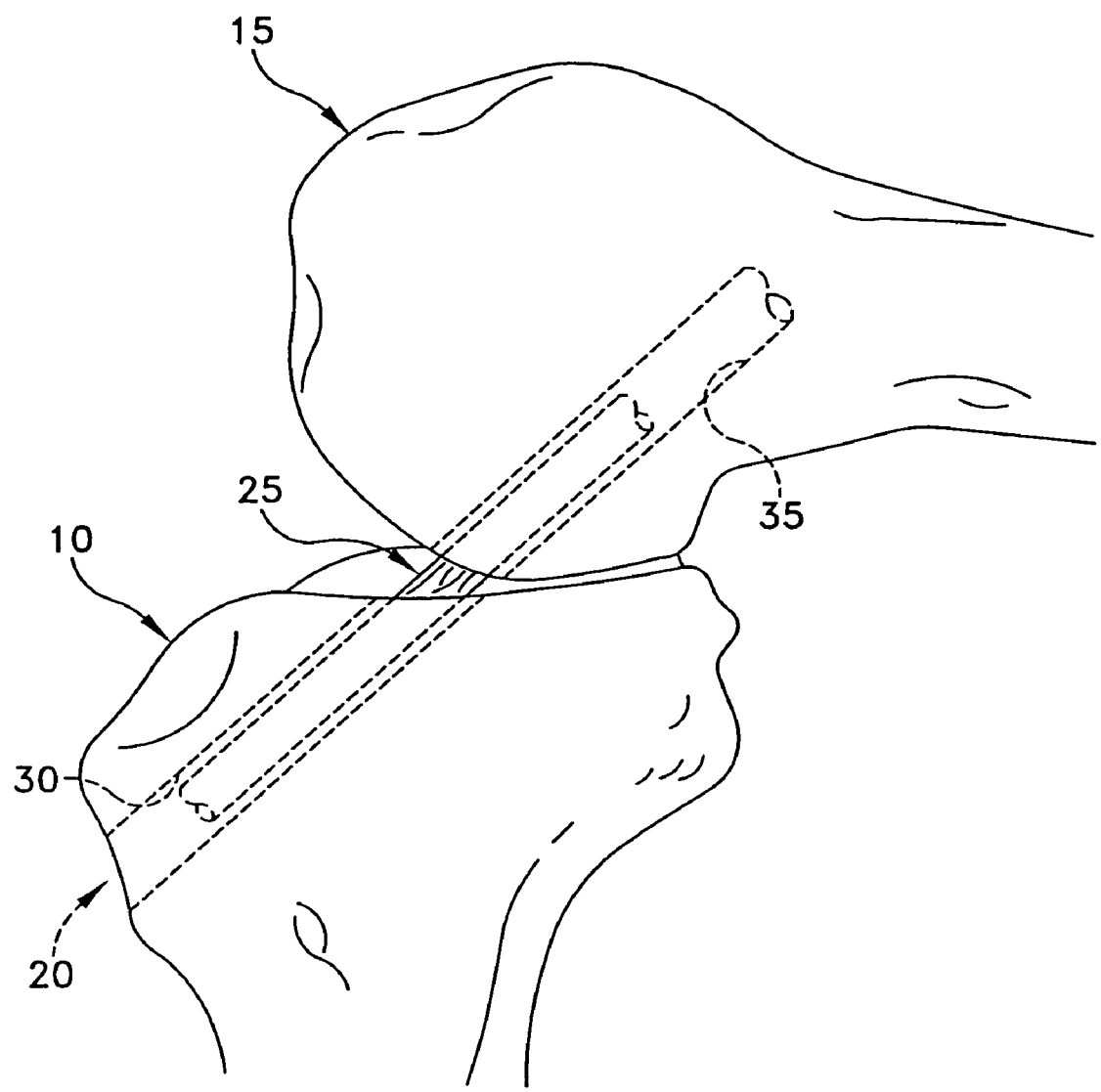
FIG. 2 is a schematic side view of the same knee joint, except showing portions of an ACL reconstruction.
Figure 3:
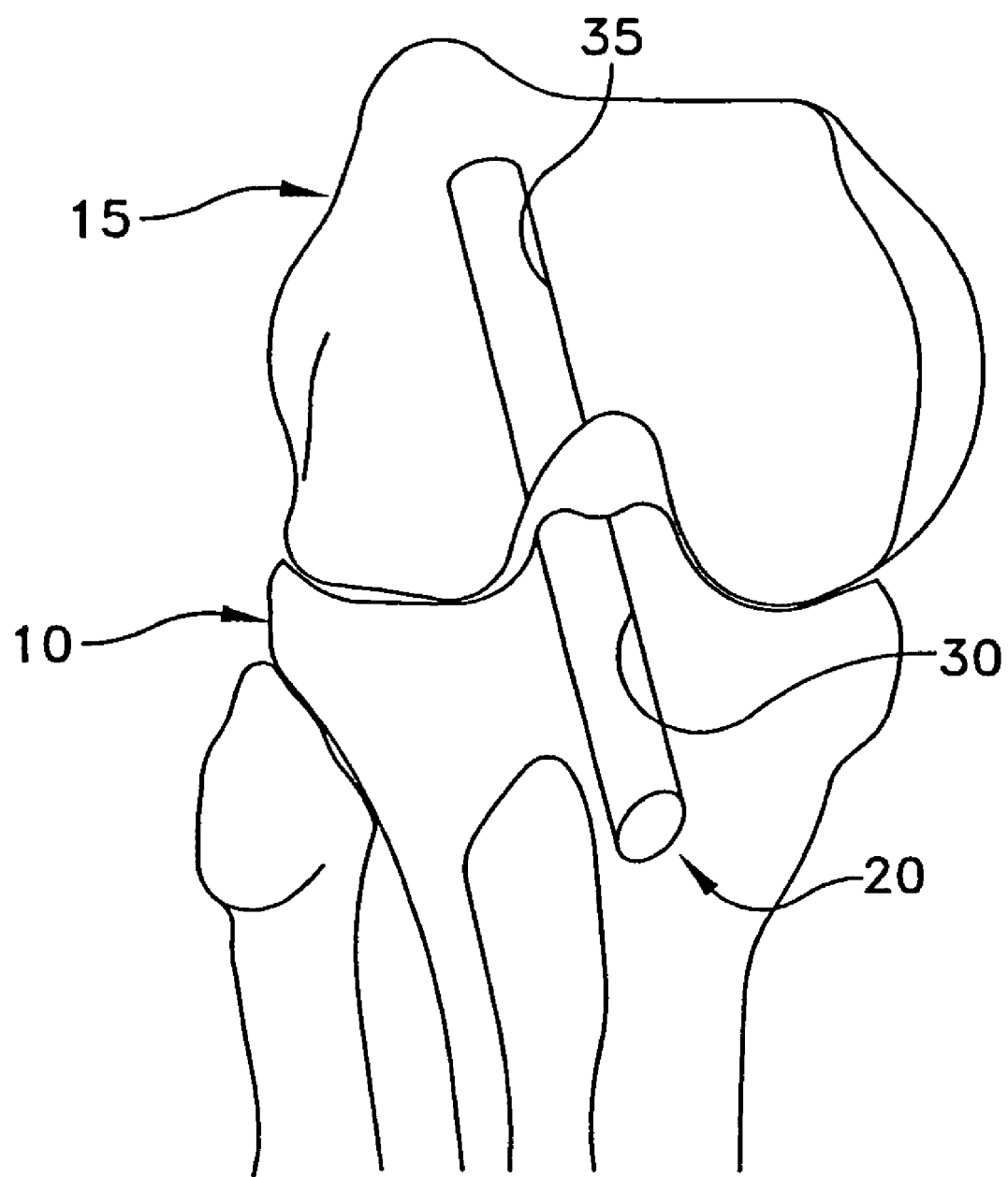
FIGS. 3, 5, 6 and 8-21 are schematic front views of a knee joint, illustrating a novel procedure for positioning a graft ligament in a bone tunnel and securing it in position.

More particularly, and looking now at FIG. 3, the bone tunnel 20 is first formed by drilling through tibia 10 and up into femur 15, whereby to form tibial tunnel 30 and femoral tunnel 35. This is done with conventional ACL drilling apparatus of the sort well known in the art.

Figure 4:
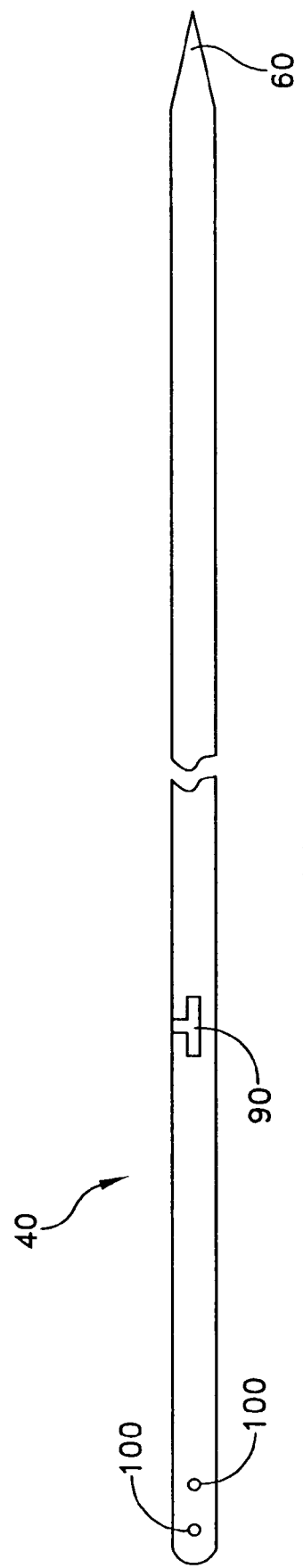
FIG. 4 is a schematic side view of a passing pin used in a preferred form of the invention.
Figure 5:
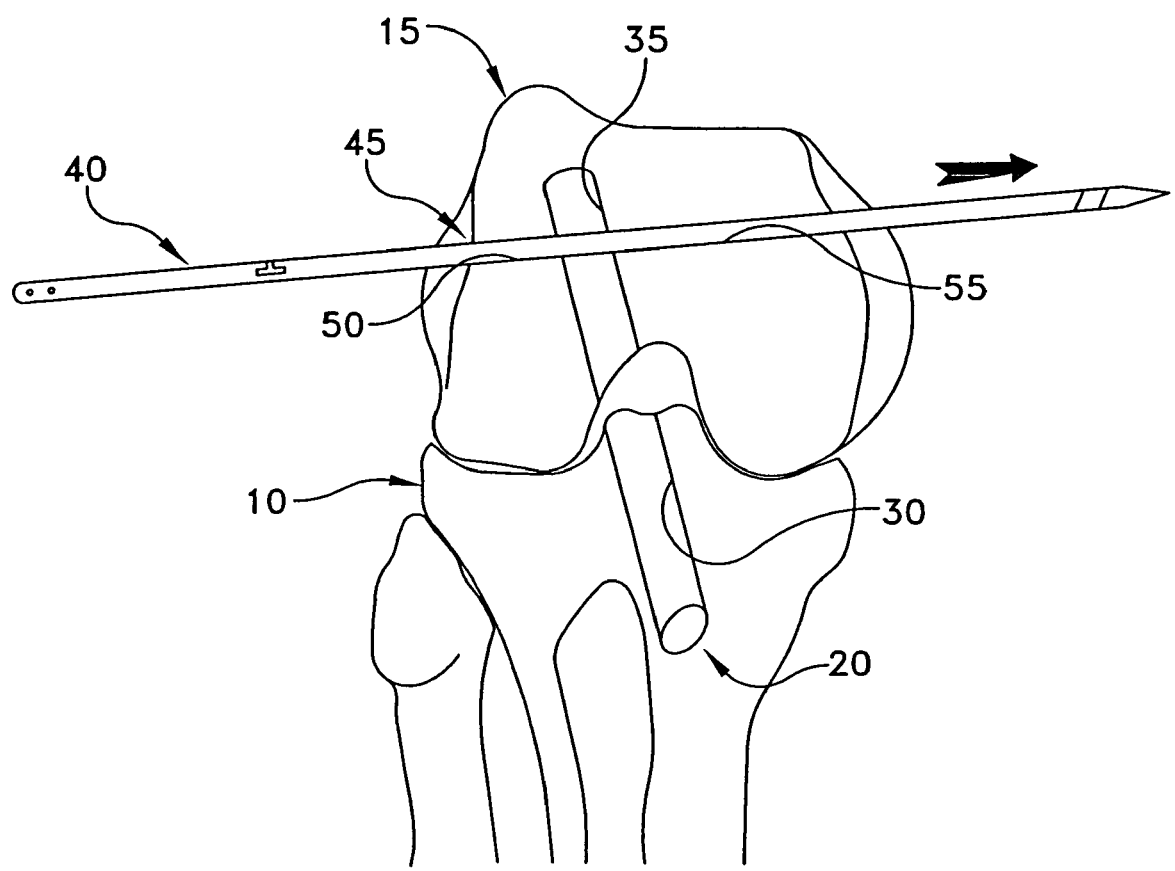
Figure 6:
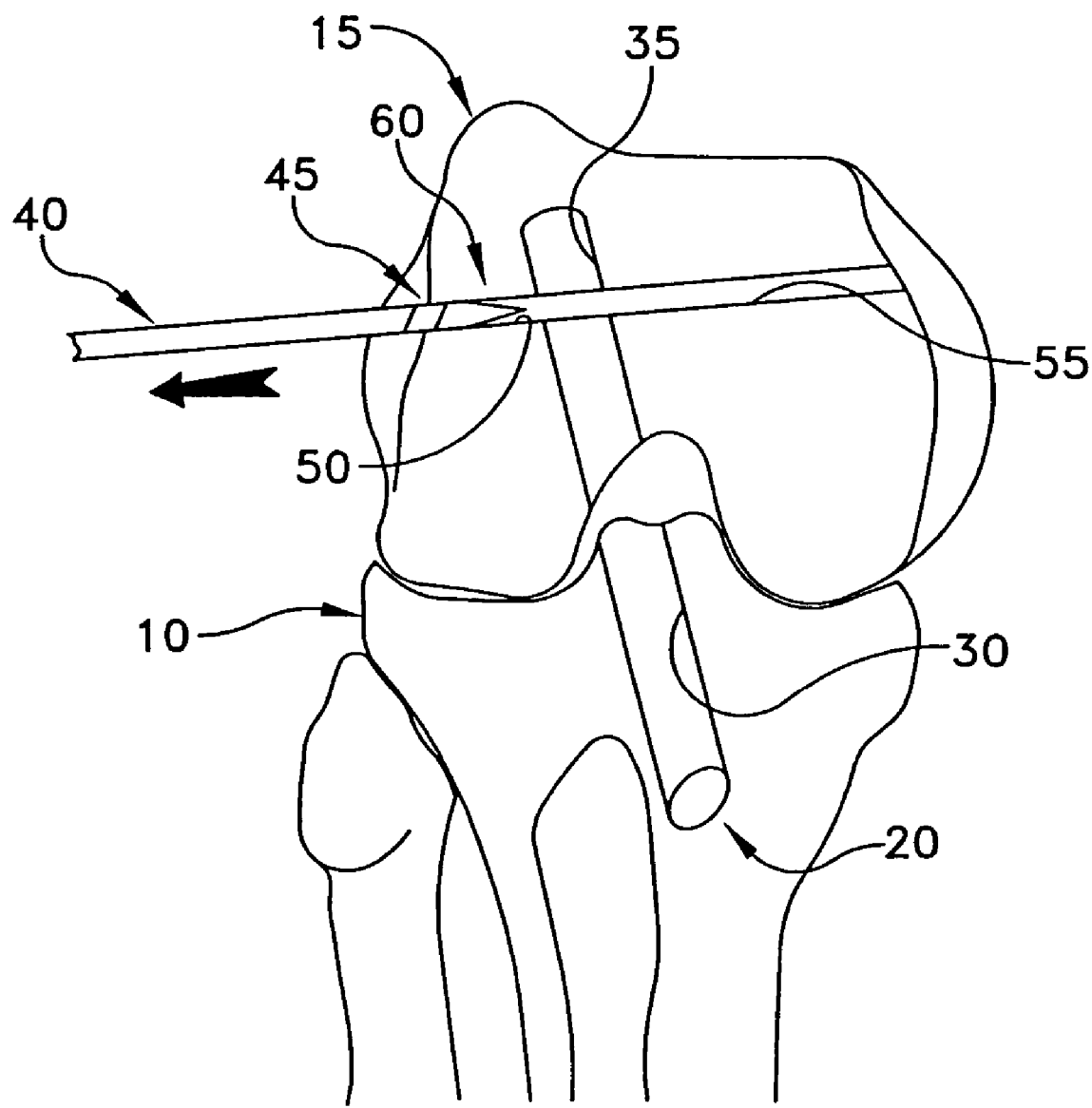

Next, a transverse bone tunnel is formed in femur 15 so that the transverse bone tunnel intersects femoral tunnel 35. This is preferably done using a passing pin 40 such as that shown in FIG. 4. Passing pin 40 is drilled transversely across femoral bone tunnel 35 (FIG. 5) so as to produce the transverse bone tunnel 45. Bone tunnel 20 effectively bifurcates transverse bone tunnel 45 into two tunnel portions, a first transverse bone tunnel portion 50 and a second transverse bone tunnel portion 55. After transverse bone tunnel 45 has been formed, passing pin 40 is retracted within transverse bone tunnel 45 so that the leading tip 60 of passing pin 40 is located in first transverse bone tunnel portion 50 (FIG. 6).

Figure 7:
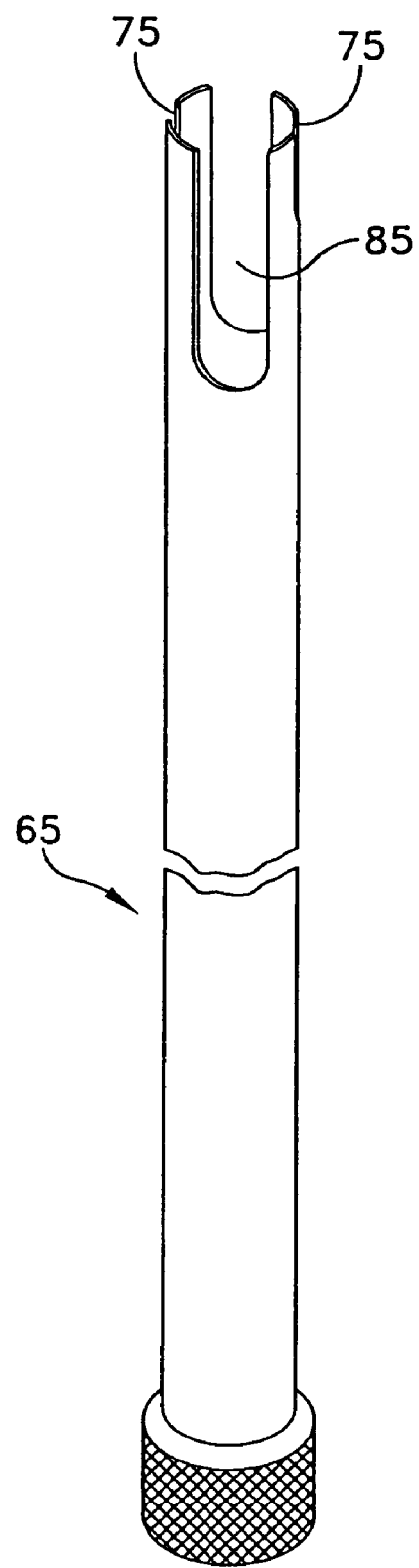
FIG. 7 is a schematic perspective view of an inserter used in a preferred form of the invention.
Figure 8:
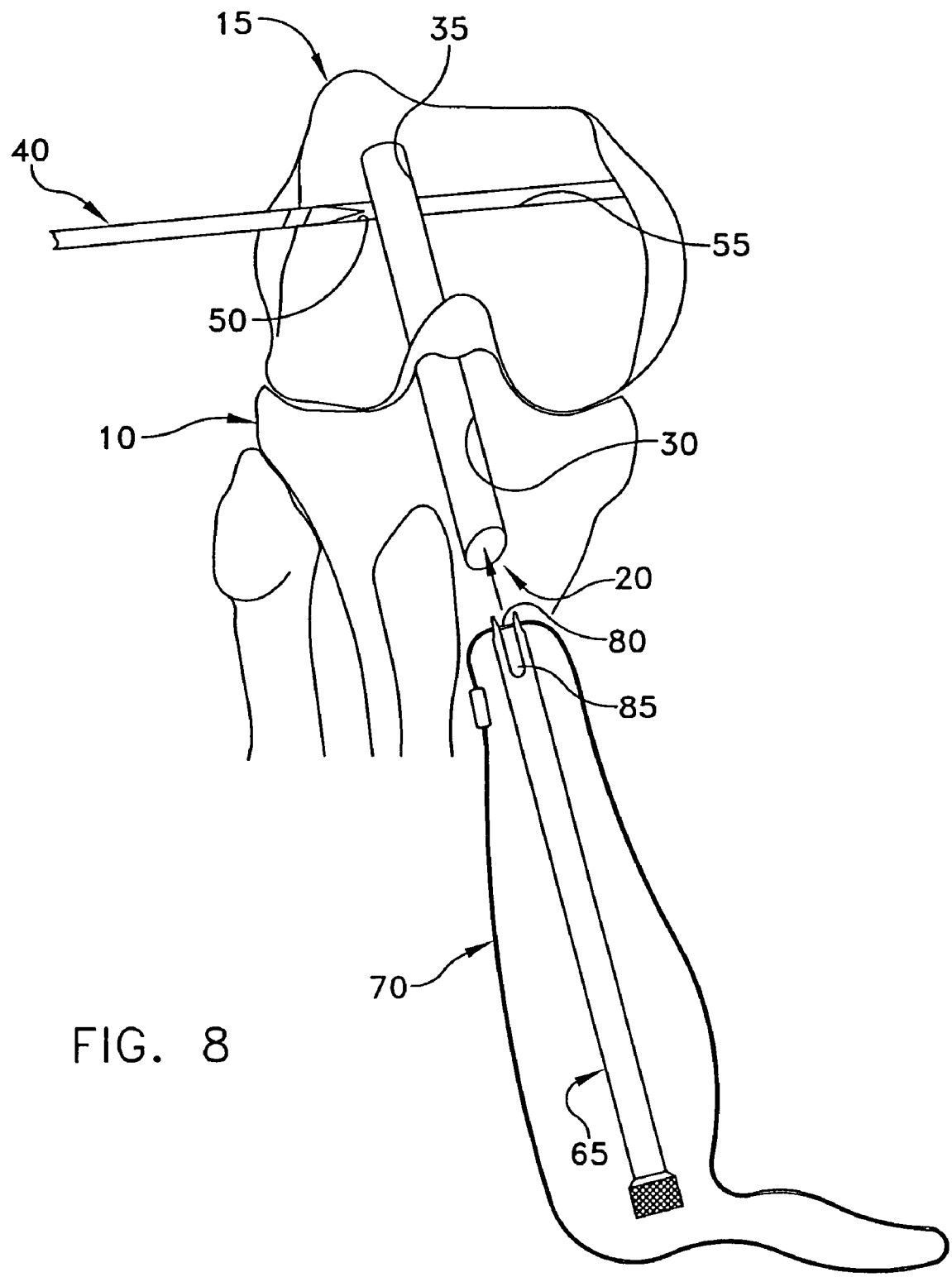
Figure 9:
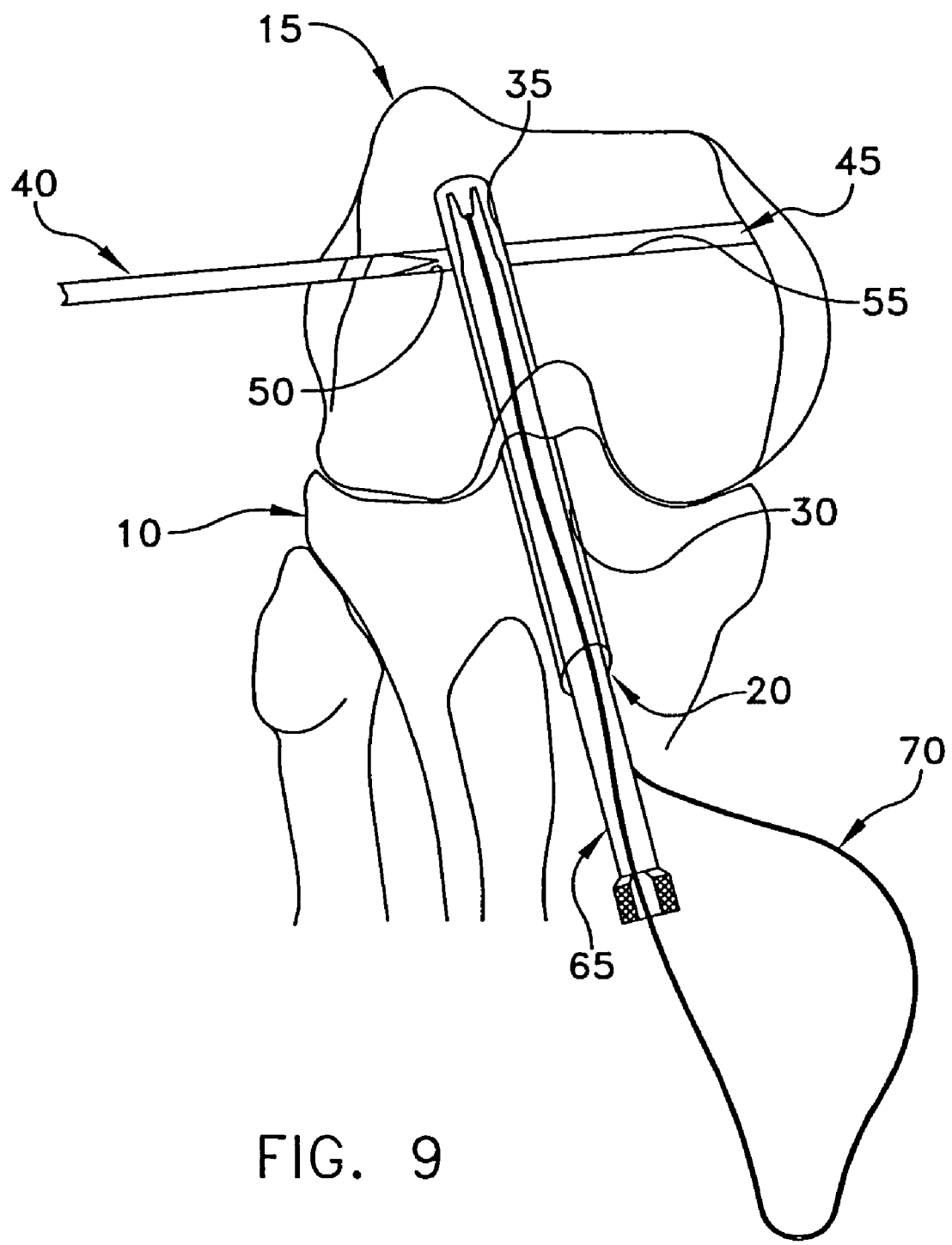

Once transverse bone tunnel 45 has been formed and passing pin 40 has been backed off so that its leading tip 60 is in first transverse bone tunnel portion 50, a flexible member is passed up bone tunnel 20. This is preferably done using an inserter 65 such as that shown in FIG. 7. More particularly, the flexible member 70 (FIG. 8) is initially in the form of a closed loop. This closed loop is slipped into a pair of diametrically-opposed grooves 75 (FIG. 7) located at the distal end of inserter 65. As a result, a segment 80 (FIG. 8) of flexible member 70 is suspended across a diametrically-extending channel 85 (FIGS. 7 and 8) formed in the distal end of inserter 65. Then the distal end of inserter 65 is passed up tibial tunnel 30, across the interior of the knee joint, and then up femoral tunnel 35 (FIG. 9). Inserter 65 is pushed far enough up femoral tunnel 35 so that the aforementioned segment 80 of flexible member 70 is positioned on the distal side of transverse bone tunnel 45, with channel 85 of inserter 65 being aligned with transverse bone tunnel 45.

Figure 10:
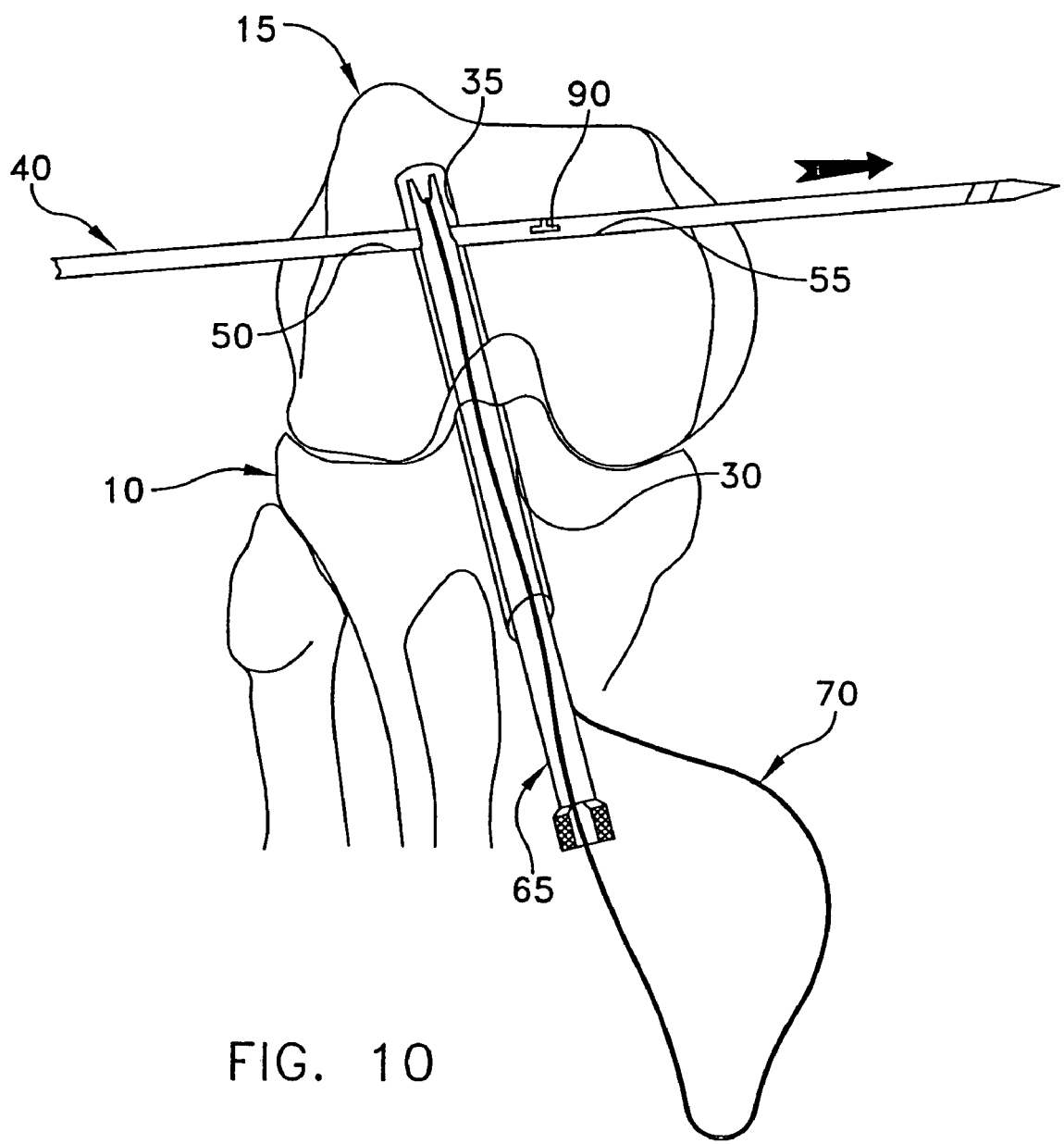
Figure 11:
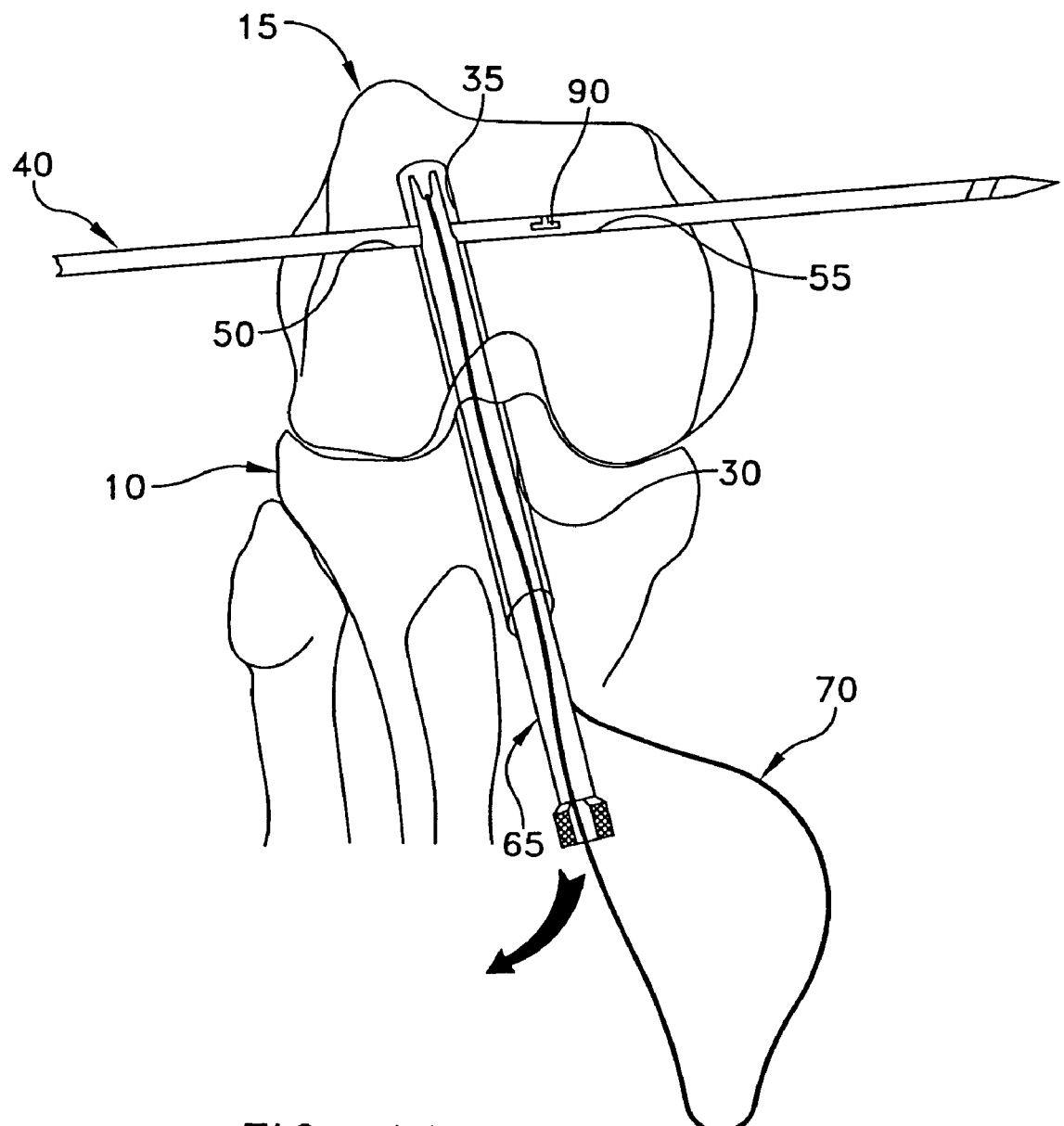
Figure 12:
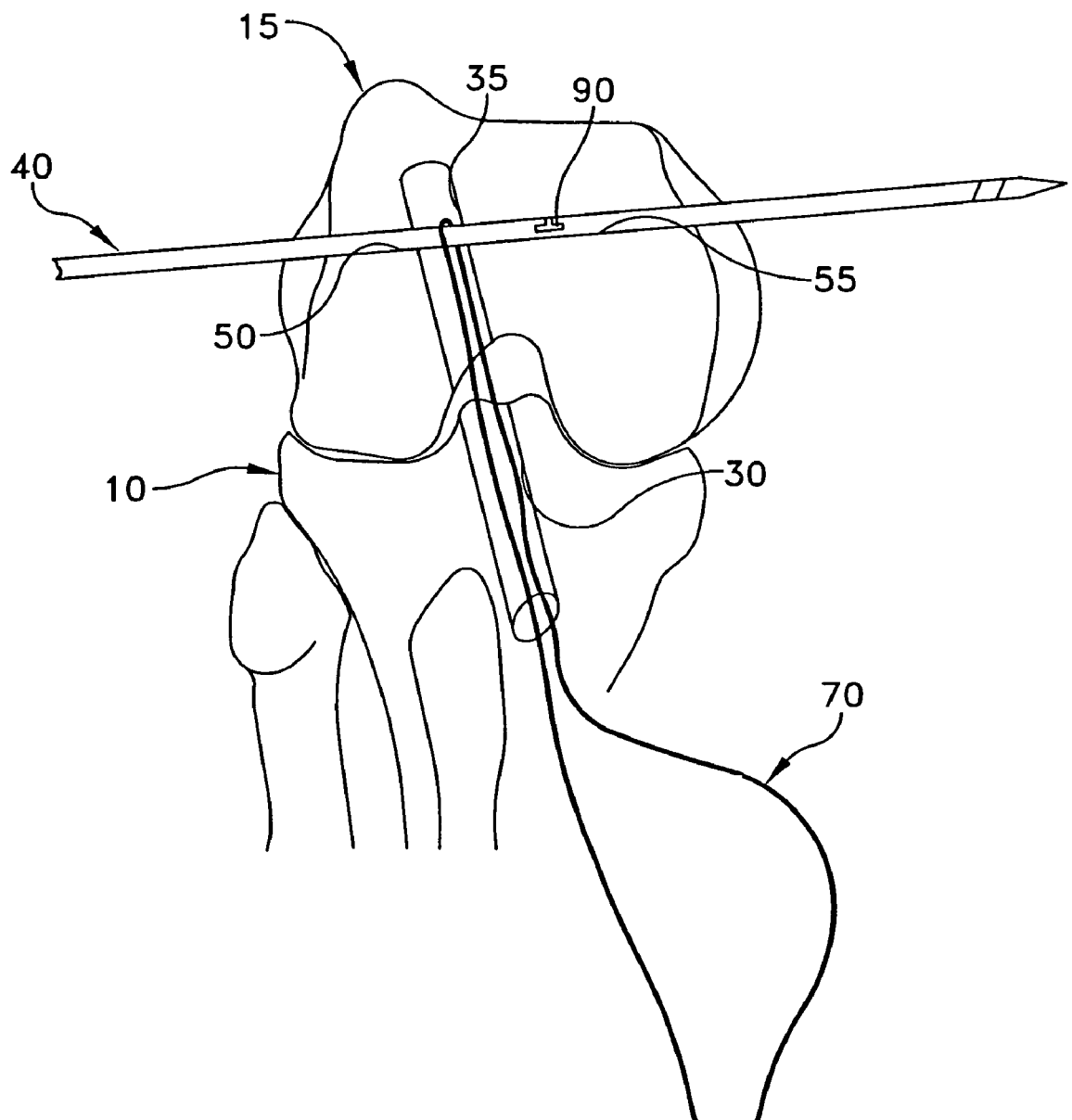

Next, passing pin 40 is advanced in transverse bone tunnel 45 so that the passing pin passes through channel 85 in inserter 65 and beneath segment 80 of flexible member 70 (FIG. 10). Passing pin 40 is advanced far enough so that its notch 90 (FIG. 4) is on the distal side of inserter 65 (FIG. 10). Then inserter 65 is retracted proximally so that segment 80 of flexible member 70 is brought into engagement with, and is supported by, the top of passing pin 40 (FIG. 11). Inserter 65 is preferably fully withdrawn from bone tunnel 20 at this point (FIG. 12).

Figure 13:
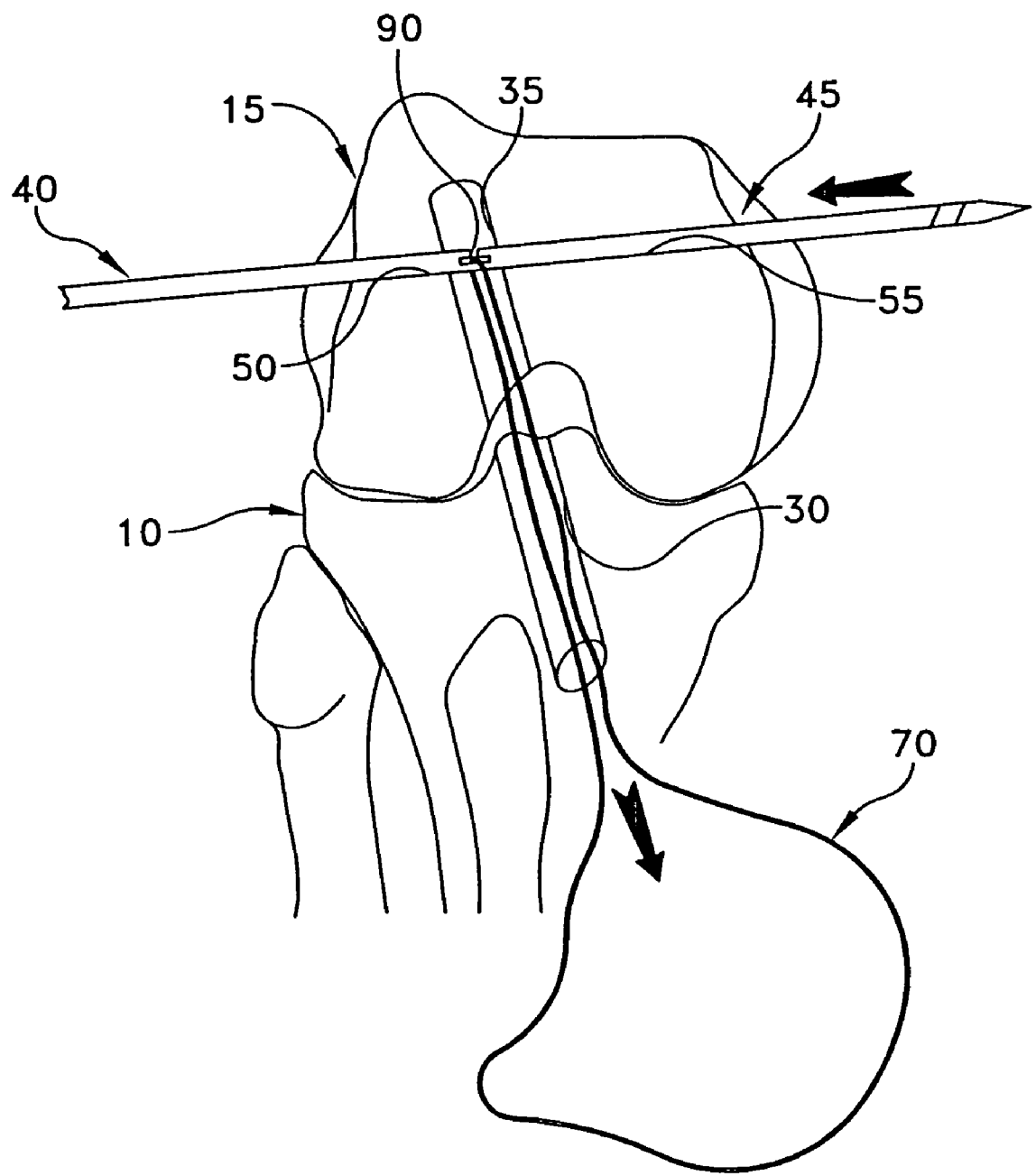
Figure 14:
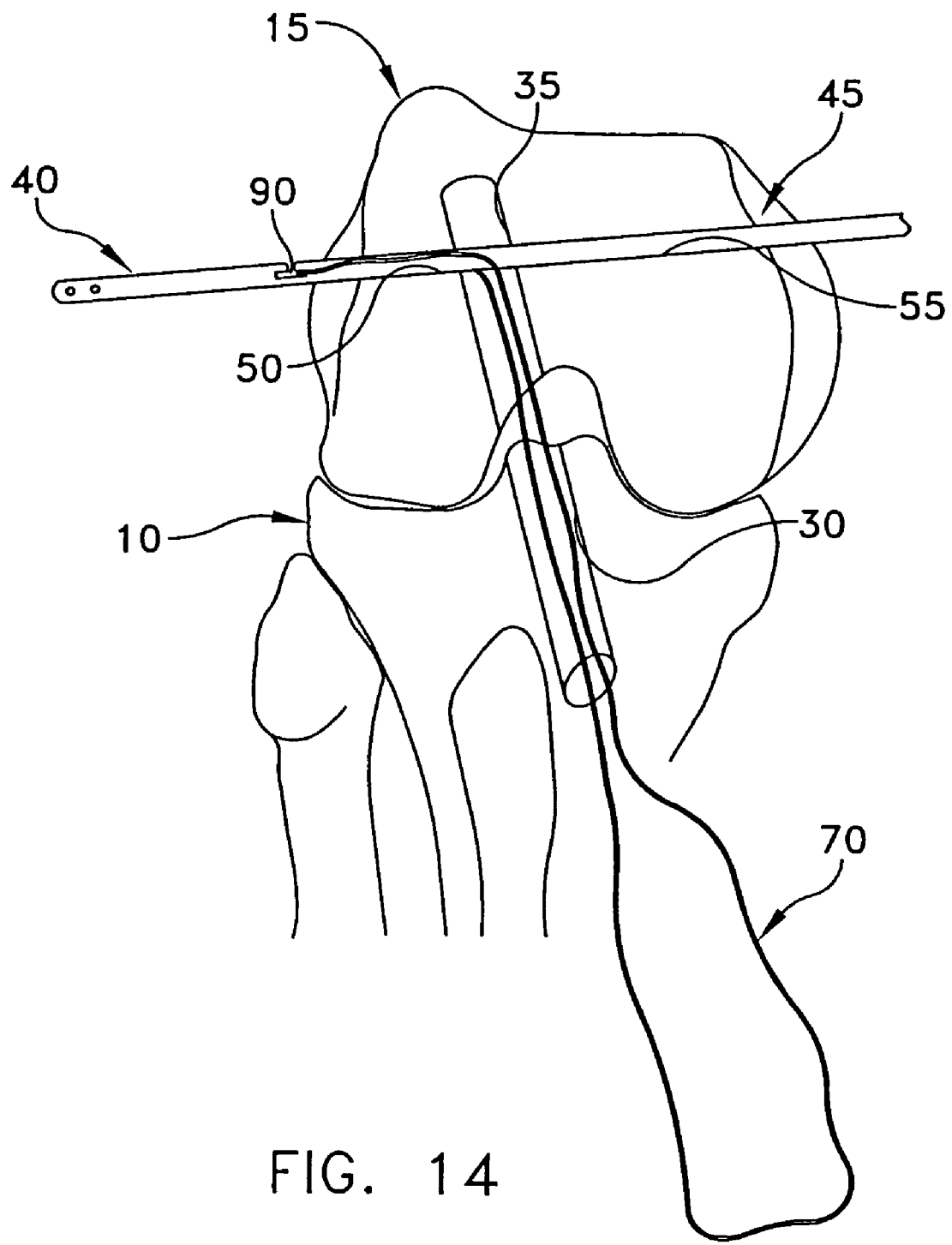

Next, as slight downward pressure is applied to flexible member 70, passing pin 40 is retracted until flexible member 70 slips into, and is captured by, notch 90 of passing pin 40 (FIG. 13). Then passing pin 40 is retracted further out of transverse bone tunnel 45, until its notch 90 (and hence flexible member 70) is free of transverse bone tunnel 45 (FIG. 14).

At this point, the closed loop of flexible member 70 extends into first transverse bone tunnel portion 50, down femoral tunnel 35, across the interior of the knee joint, down tibial tunnel 30, and out the front of tibia 10.

Figure 15:
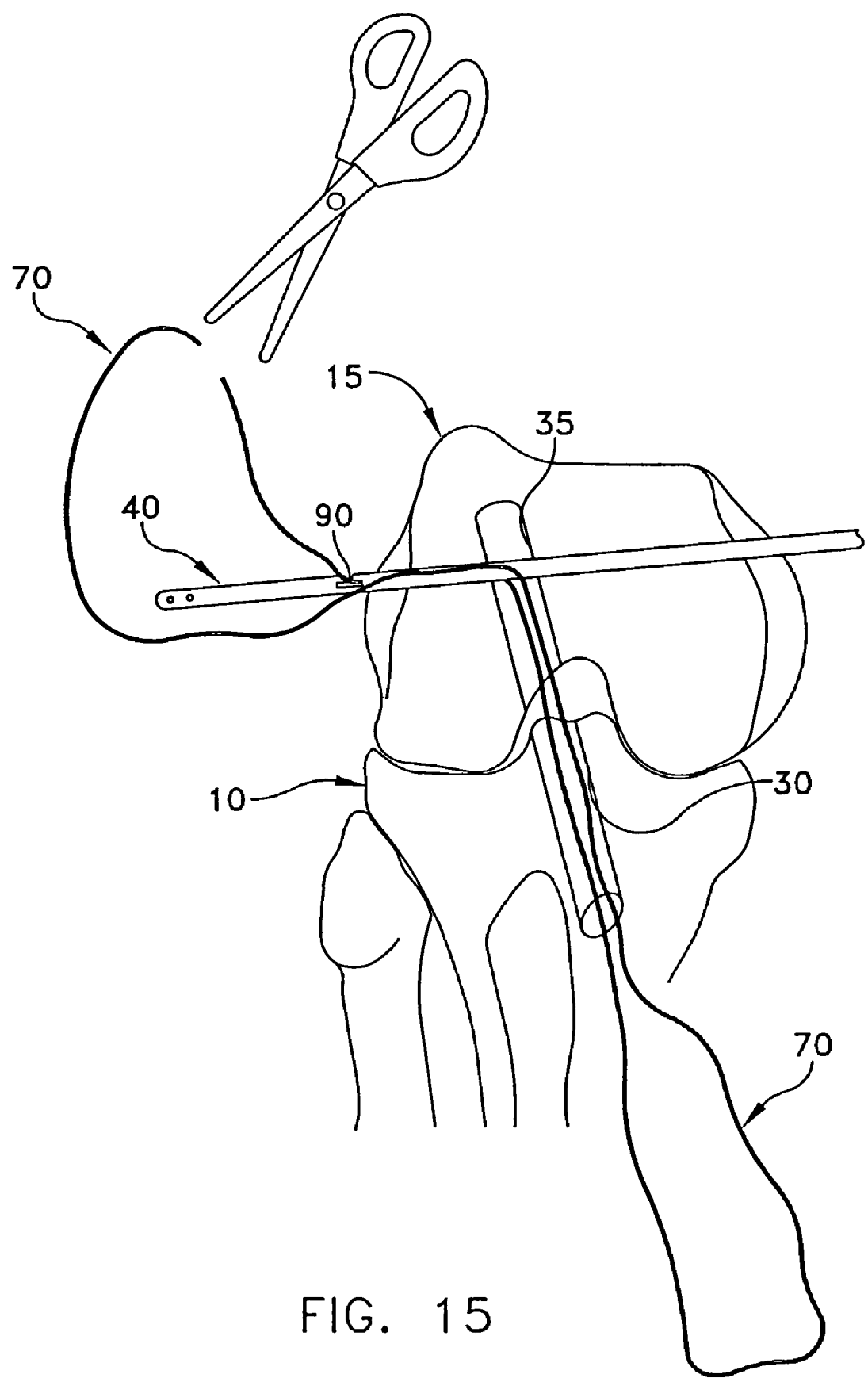
Figure 16:
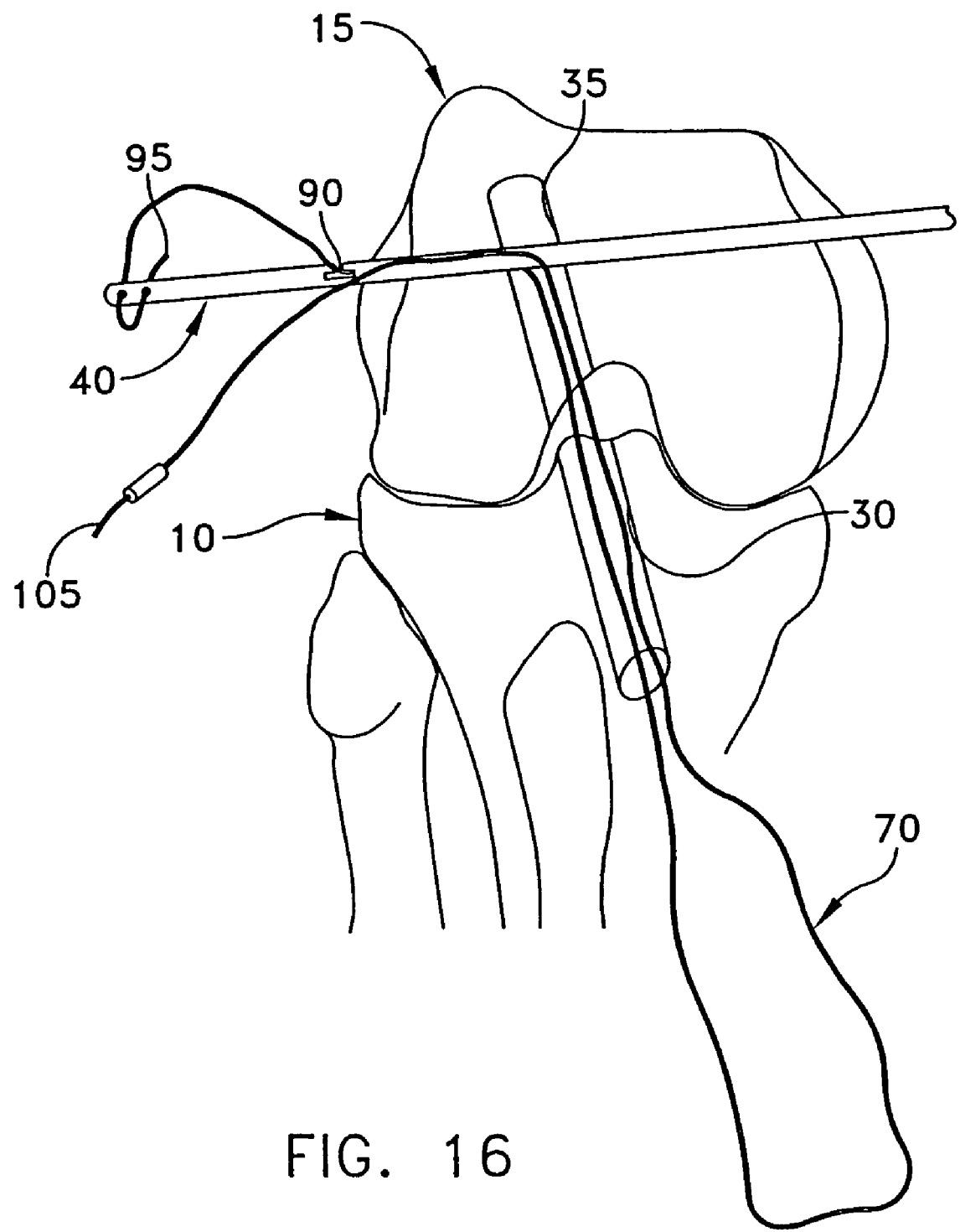

Next, the closed loop of flexible member 70 is withdrawn from notch 90 of passing pin 40, and then flexible member 70 is cut (FIG. 15). Then, one free end 95 of flexible member 70 is attached to passing pin 40 (FIG. 16) by passing that free end 95 through one or more holes 100 (FIG. 4) formed in the proximal end of passing pin 40. The other free end 105 (FIG. 16) of flexible member 70 is left hanging outside the joint.

Figure 17:
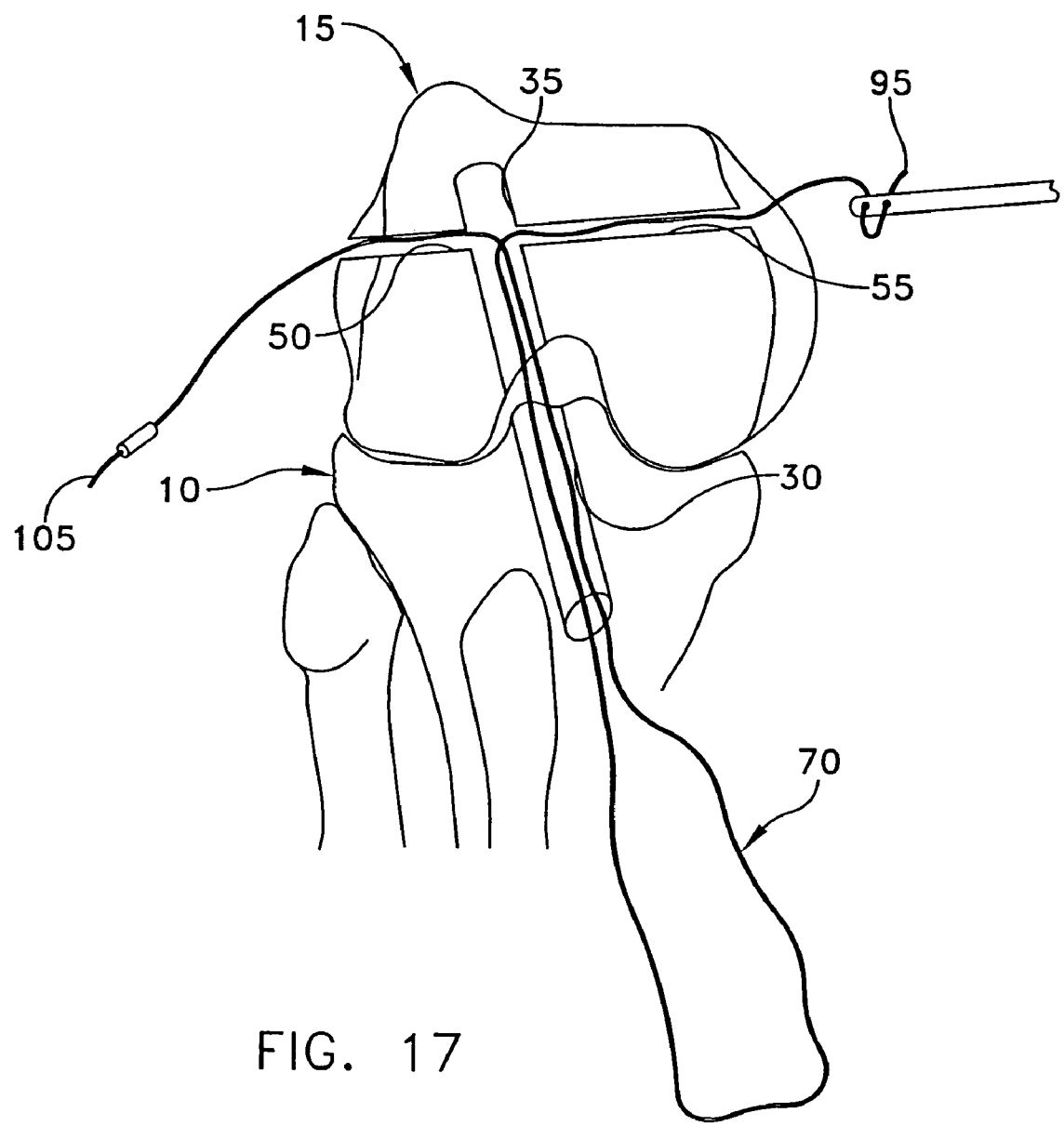
Figure 18:
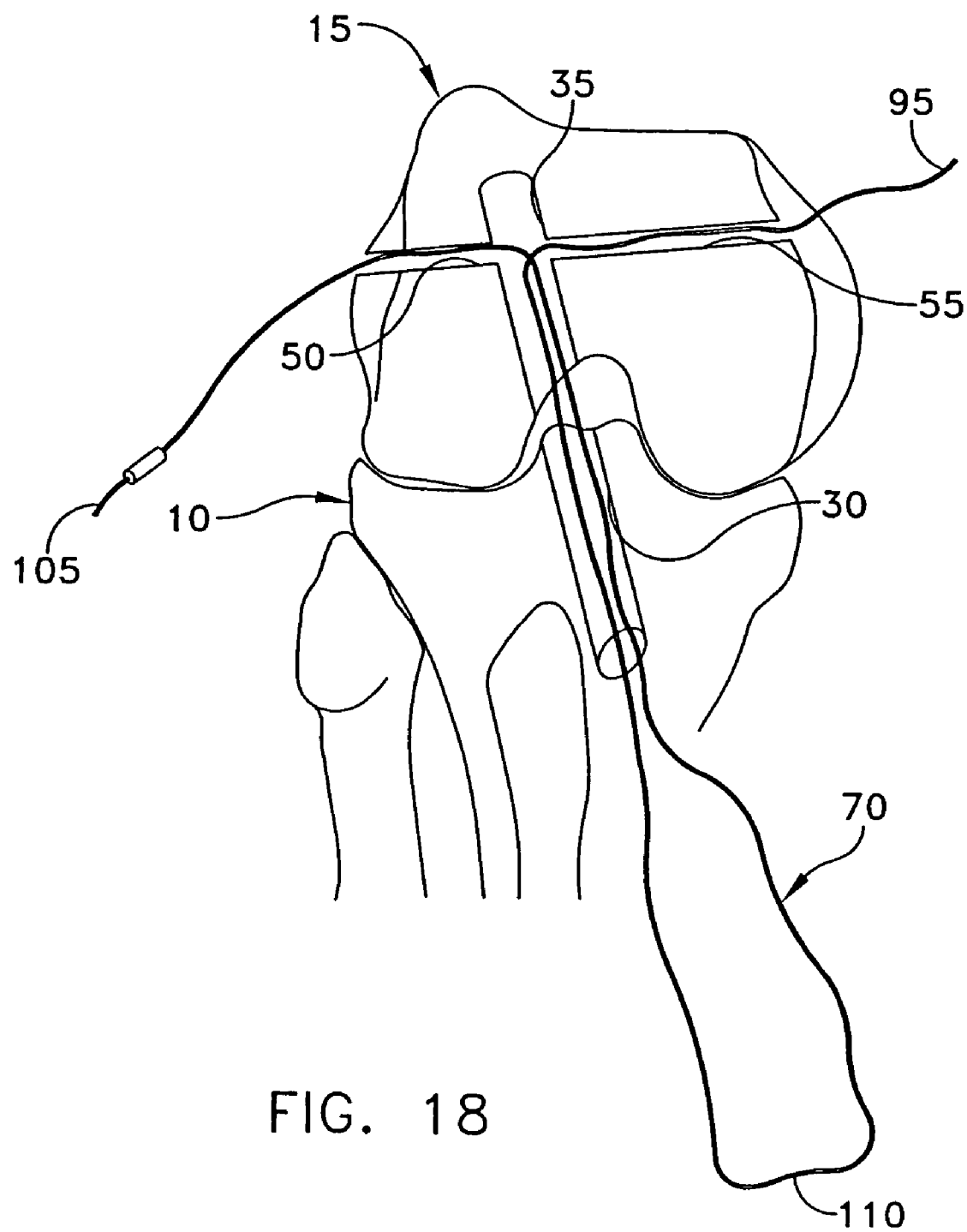

Next, passing pin 40 is passed completely through femur 15 (FIG. 17), carrying the free end 95 of flexible member 70 with it. Free end 95 of flexible member 95 is then dismounted from passing pin 40 (FIG. 18).

At this point flexible member 70 extends into first transverse bone tunnel portion 50, down femoral tunnel 35, across the interior of the knee joint, down tibial tunnel 30, forms a loop 110 outside the front of tibia 10, extends back up tibial tunnel 30, across the interior of the knee joint, back up femoral tunnel 35, and then out second transverse bone tunnel portion 55.

Figure 19:
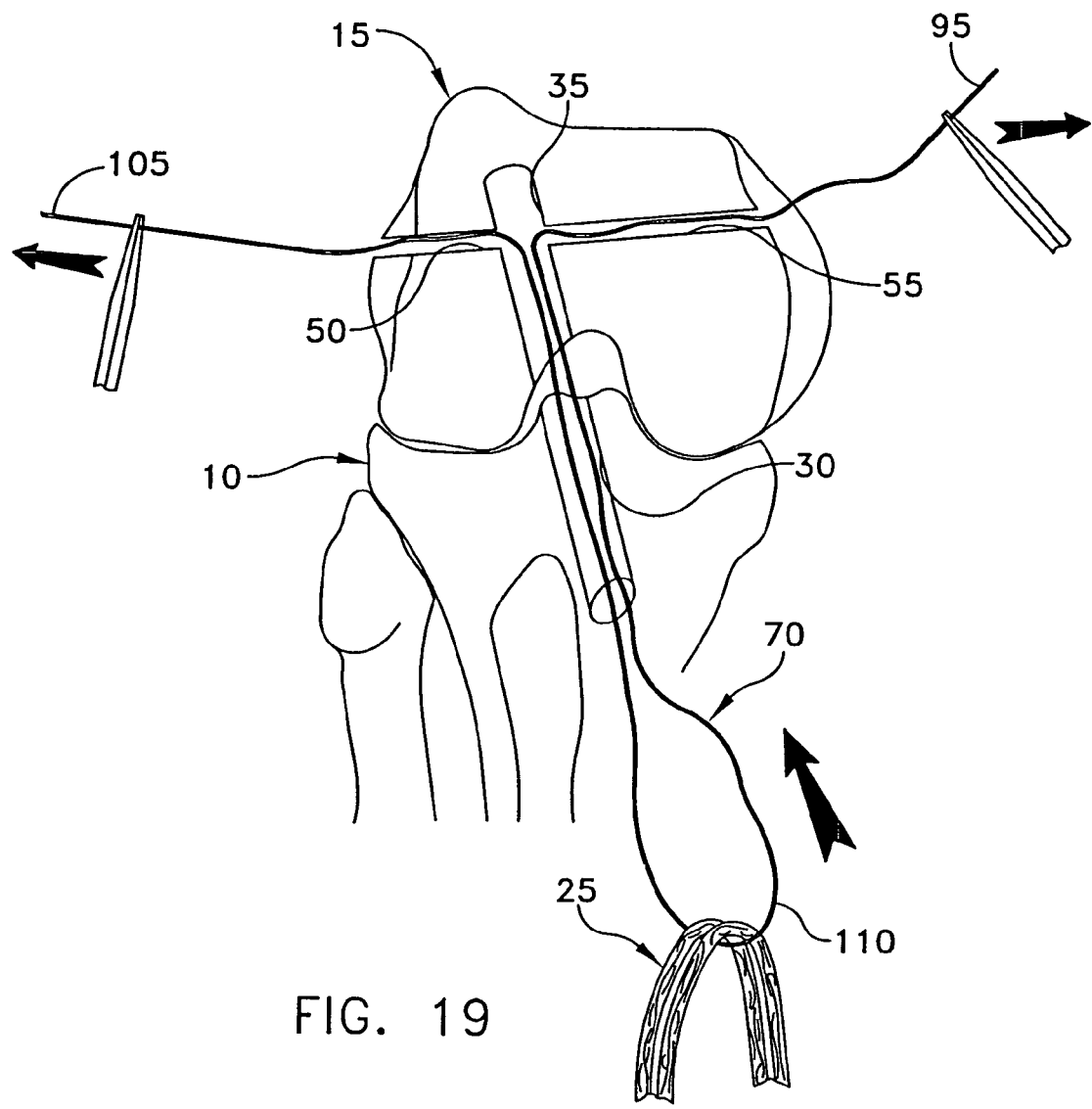
Figure 20:
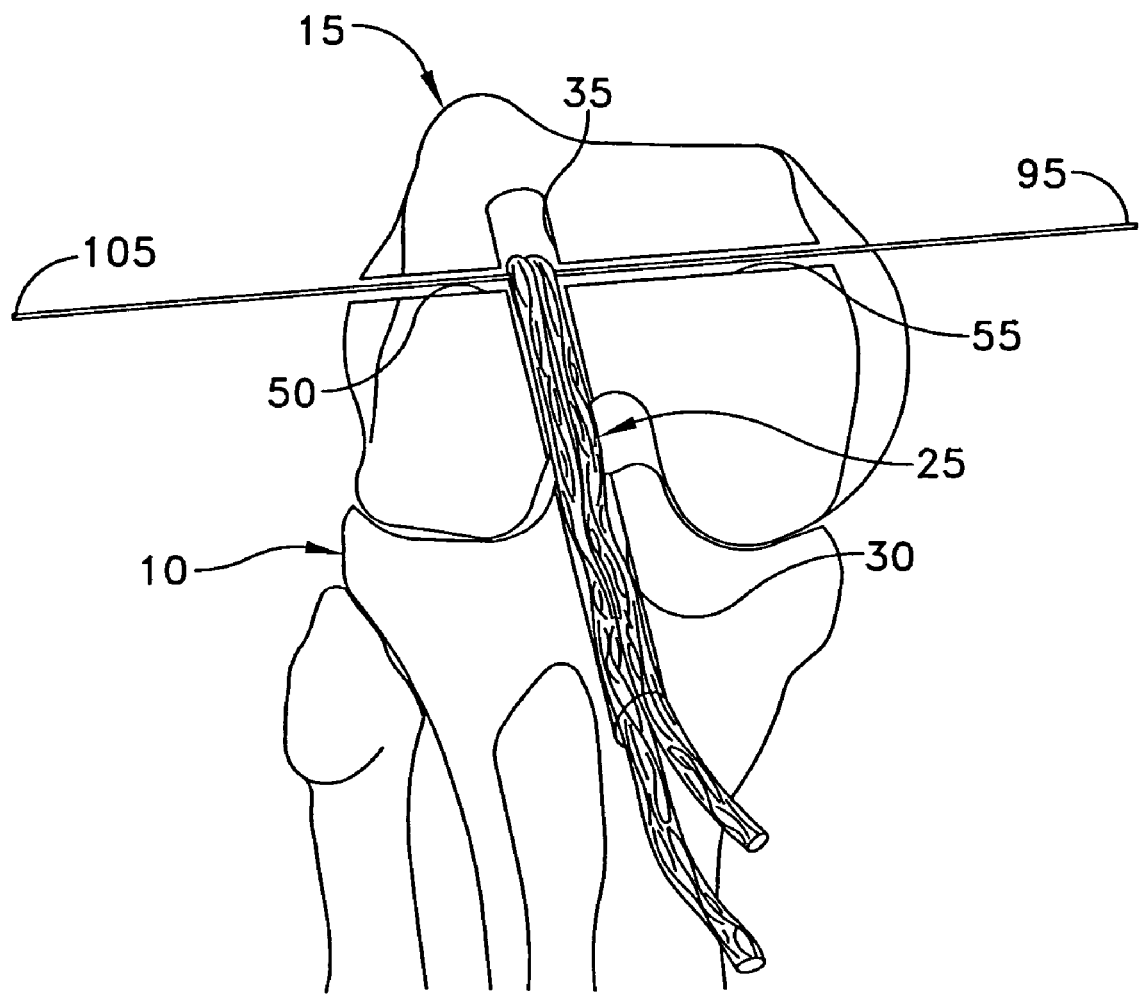

Next, and looking now at FIG. 19, the graft ligament 25 is looped through loop 110 of flexible member 70. First and second ends 95, 105 of flexible member 70 are then pulled outboard, away from femur 15, in the manner shown in FIG. 19, whereby to pull loop 110 of flexible member 70, and hence graft ligament 25, up tibial tunnel 30, across the interior of the knee joint, and up femoral tunnel 35 so as to achieve the position shown in FIG. 20.

Figure 21:
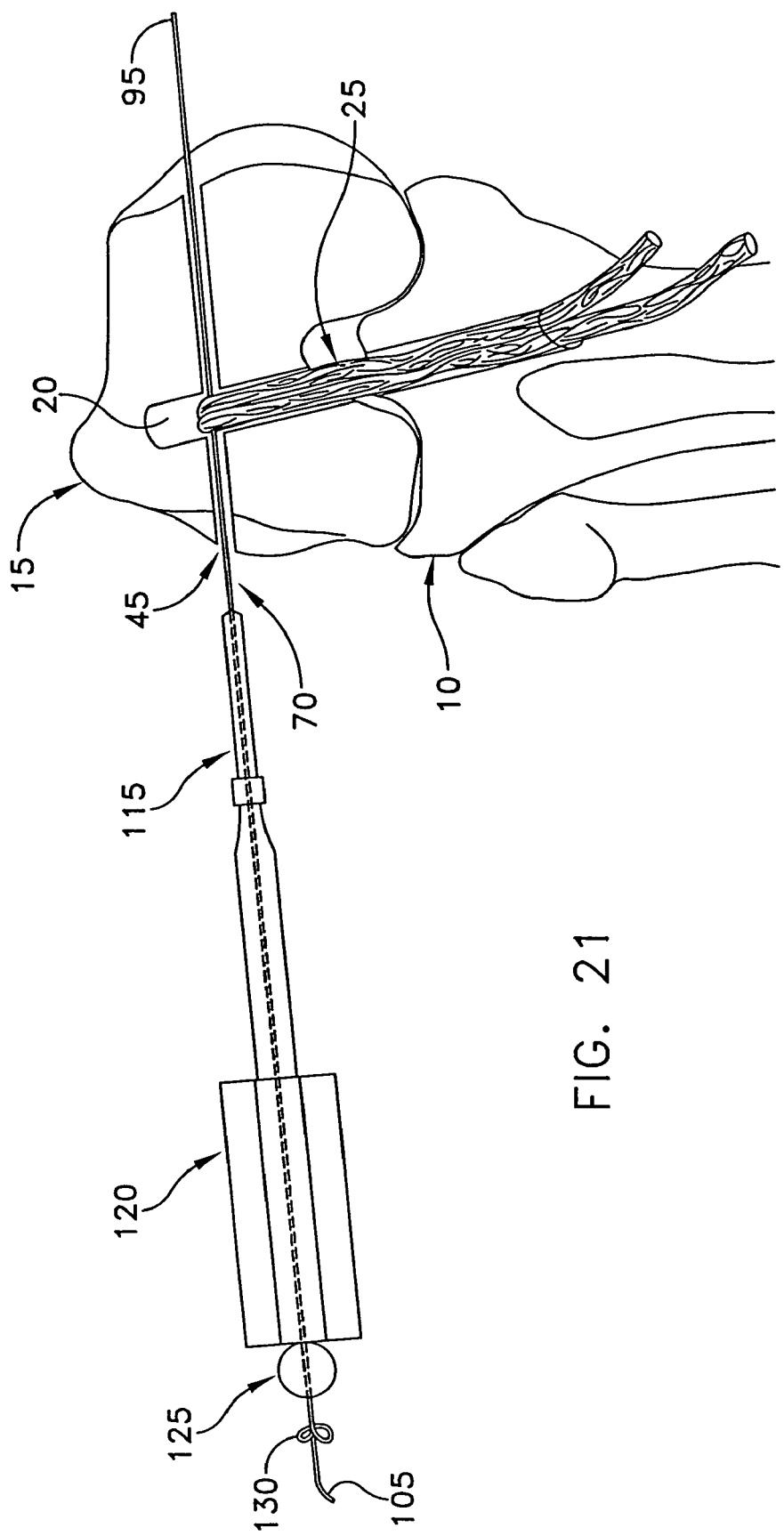

Looking next at FIG. 21, flexible member 70 is then used as a guide to pass a cannulated crosspin 115 through transverse bone tunnel 45 and, in the process, beneath looped graft ligament 25, whereby to support graft ligament 25 within bone tunnel 20. A cannulated driver 120 may be used to set cannulated crosspin 115 in transverse bone tunnel 45. It will be appreciated that flexible member 70 should be held under tension while cannulated crosspin 115 is deployed in femur 15 so as to provide proper guidance for cannulated crosspin 115. This can be achieved by simultaneously pulling on the two free ends, 95 and 105, of flexible member 70 and then turning cannulated driver 120. However, it will be appreciated that this technique requires three hands: one for pulling on free end 95, one for pulling on free end 105, and one for turning cannulated driver 120. In some instances, it may be desirable to use only two hands. To this end, in one preferred form of the invention, a cannulated bead 125 may be set on flexible member 70, adjacent free end 105, and then a knot 130 formed in the flexible member proximal to the cannulated bend. This construction allows a surgeon to maintain tension on flexible member 70 by pulling, with one hand, on the free end 95 while using the other hand to turn cannulated driver 120. Once cannulated crosspin 115 has been deployed in femur 115, flexible member 70 may be removed from transverse bone tunnel 45, e.g., by pulling proximally on bead 125.

The proximal ends of graft ligament 25 may thereafter be secured to tibia 10 in ways well known in the art so as to complete the ligament repair procedure.

Figure 22:
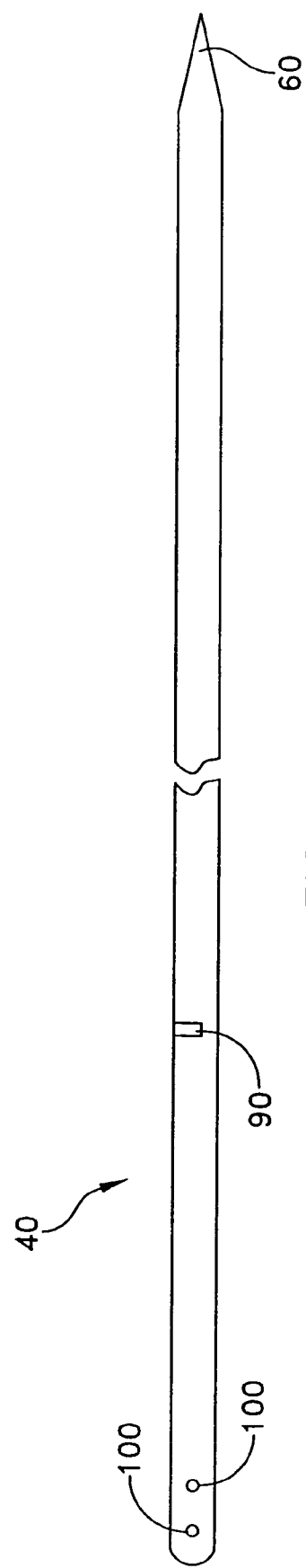
FIG. 22 is a schematic side view of another form of passing pin used in a preferred form of the invention.

It should be appreciated that notch 90 (FIG. 4) of passing pin 40 may have various configurations consistent with the present invention. Thus, for example, in FIG. 4 notch 90 is shown as having a substantially T-shaped configuration. However, other configurations may also be used. Thus, for example, and looking now at FIG. 22, notch 90 may have a substantially straight configuration. Still other configurations will be apparent to those skilled in the art in view of the present disclosure.

It is to be understood that the present invention is by no means limited to the particular construction and method steps disclosed above and/or shown in the drawings, but also comprises any modifications or equivalents within the scope of the claims.

What is claimed is:

1. A method for positioning a graft ligament in a bone tunnel, said method comprising the steps of:
   (1) forming a first bone tunnel in a bone, said first bone tunnel having a first opening at one end thereof, and forming a second bone tunnel in the same bone, said second bone tunnel being transverse to, and intersecting, said first bone tunnel, said second bone tunnel having first and second portions extending from said first bone tunnel, said first portion of said second bone tunnel having a second opening at one end thereof, and said second portion of said second bone tunnel having a third opening at one end thereof;
   (2) positioning a closed loop of a flexible member within said first bone tunnel and said first portion of said second bone tunnel such that a first portion of said closed loop extends out of said first opening and a second portion of said closed loop extends out of said second opening, parting said closed loop outside said second opening so as to create a first free end and a second free end, and passing said second free end through said second bone tunnel so that said second free end extends out of said third opening, and positioning the graft ligament over a portion of said flexible member extending out of said first opening; and
   (3) pulling said first and second free ends of said flexible member so as to draw said graft ligament into said first bone tunnel.

2. A method according to claim 1 wherein said closed loop of said flexible member is positioned in said first bone tunnel and said first portion of said second bone tunnel by mounting said closed loop of said flexible member onto an inserter, passing said inserter into said first opening of said first bone tunnel, up said first bone tunnel until said first portion of the closed loop is located at the intersection of said second bone tunnel with said first bone tunnel, and pulling said first portion of said closed loop through said first portion of said second tunnel and out said second opening.

3. A method according to claim 2 wherein said inserter comprises a shaft having a diametrically-extending channel formed in the distal end thereof.

4. A method according to claim 3 wherein said inserter has a pair of diametrically-opposing grooves on either side of said channel.

5. A method according to claim 2 wherein a passing pin is used to pull said first portion of said closed loop through said first portion of said second bone tunnel and out of said second opening.

6. A method according to claim 5 wherein said passing pin comprises a notch for releasably capturing said flexible member.

* * * * *